United States Patent
Luhrs

(10) Patent No.: US 8,348,901 B2
(45) Date of Patent: Jan. 8, 2013

(54) NASAL DEVICE AND METHOD OF POSITIONING NASOGASTRIC TUBING WITHIN A PATIENT

(76) Inventor: Reba Luhrs, Kirkwood, MO (US)

( * ) Notice: Subject to any disclaimer, the term of this patent is extended or adjusted under 35 U.S.C. 154(b) by 355 days.

(21) Appl. No.: 12/617,340

(22) Filed: Nov. 12, 2009

(65) Prior Publication Data

US 2010/0121281 A1 May 13, 2010

Related U.S. Application Data

(60) Provisional application No. 61/114,226, filed on Nov. 13, 2008.

(51) Int. Cl.
*A61M 25/02* (2006.01)
(52) U.S. Cl. ........................ 604/180; 604/174
(58) Field of Classification Search ............. 128/203.22, 128/206.11, 207.18; 604/94.01, 174, 179, 604/180, 516; 606/196, 199
See application file for complete search history.

(56) References Cited

U.S. PATENT DOCUMENTS

| | | | |
|---|---|---|---|
| 3,972,321 A | 8/1976 | Proctor | |
| 4,114,626 A | 9/1978 | Beran | |
| 4,120,304 A | 10/1978 | Moor | |
| 4,156,426 A | 5/1979 | Gold | |
| 4,648,398 A | 3/1987 | Agdanowski et al. | |
| 4,736,741 A | 4/1988 | Payton et al. | |
| 4,932,943 A * | 6/1990 | Nowak | 604/180 |
| 4,986,815 A | 1/1991 | Schneider | |
| 5,105,807 A | 4/1992 | Kahn et al. | |
| 5,185,005 A | 2/1993 | Ballantyne | |
| 5,308,339 A | 5/1994 | Kalt et al. | |
| 5,364,367 A | 11/1994 | Banks et al. | |
| 5,462,528 A | 10/1995 | Roewer | |
| 5,752,511 A * | 5/1998 | Simmons et al. | 128/207.18 |
| 5,827,224 A | 10/1998 | Shippert | |
| 5,890,486 A * | 4/1999 | Mitra et al. | 128/200.24 |
| 6,093,169 A | 7/2000 | Cardoso | |
| 6,328,038 B1 * | 12/2001 | Kessler et al. | 128/207.18 |
| 6,561,193 B1 | 5/2003 | Noble | |
| 6,669,712 B1 * | 12/2003 | Cardoso | 606/199 |
| 6,837,238 B2 * | 1/2005 | McDonald | 128/200.28 |
| 7,022,890 B2 | 4/2006 | Sessions | |
| 2005/0092328 A1 | 5/2005 | Herrick et al. | |
| 2006/0283464 A1 * | 12/2006 | Dunlap | 128/207.18 |
| 2007/0277831 A1 | 12/2007 | Luhrs | |
| 2009/0306626 A1 * | 12/2009 | Sinha et al. | 604/516 |

FOREIGN PATENT DOCUMENTS

EP 331392 A2 9/1989

OTHER PUBLICATIONS

PCT International Search Report for PCT/US07/70087 dated May 9, 2008.
PCT Written Opinion for PCT/US07/70087 dated May 9, 2008.

* cited by examiner

*Primary Examiner* — (Jackie) Tan-Uyen T. Ho
*Assistant Examiner* — Gerald Landry, II
(74) *Attorney, Agent, or Firm* — Armstrong Teasdale LLP

(57) ABSTRACT

A nasal device for positioning nasogastric tubing within a patient's nose. The nasal device comprises a nasal adapter having a lumen disposed there through for guiding the nasogastric tubing within the nasal adapter. The device further comprises an adhesive member that removeably surrounds a portion of the patient's nose. The body has a front side and a back side wherein the back side contacts against the patient's nose.

18 Claims, 3 Drawing Sheets

NASAL DEVICE AND METHOD OF POSITIONING NASOGASTRIC TUBING WITHIN A PATIENT

CROSS-REFERENCE TO RELATED APPLICATIONS

This application claims priority under 35 U.S.C. §119(e) to U.S. Provisional Patent Application No. 61/114,226 filed Nov. 13, 2008 and entitled "NASAL DEVICE AND METHOD OF POSITIONING NASOGASTRIC TUBING" and is incorporated herein by reference.

STATEMENT REGARDING FEDERALLY SPONSORED RESEARCH

Not Applicable.

BACKGROUND OF THE DISCLOSURE

The present disclosure relates to a nasal device, and in particular, relates to a device that supports and positions nasogastric tubing within a patient's nose.

Tubing inserted through the nasal passage of medical patients introduces oxygen, air, or other fluid treatments (liquid or gas) into the nasopharyngeal area and directly into the patient's stomach. In addition, tubing inserted through the nasal passage introduces fluids into, or extracts fluids from, the gastrointestinal tract.

Once the tubing is inserted through the nasal passage and appropriately positioned to achieve the desired treatment, health care personnel currently try to secure the nasogastric tubing to the nose. Treatments administered to the patient by the nasal tube method can require that the tubing remain secured to the patient's nose for extended periods of time such as several hours or days. For tubing placement, the inserted tubing requires a particular position for these extended periods for effective treatment.

While the inserted tubing delivers or extracts fluids, the tubing experiences reciprocal movement known as a pistoning effect. Due to the fluid movement within the tubing, the tubing moves forward and backward within the nasal membrane. To maintain appropriate health care standards and to minimize trauma and irritation to the patient, however, the nasogastric tubing requires minimal movement while the nasal tubing remains in place. Further, the tubing must be comfortably attached to, and easily detachable from, the patient to effectively deliver or retract fluids with respect to the patient. Convenience and time efficiency regarding attachment of the tubing to the patient's nose are important considerations for the health care personnel and the patient.

A common method currently used to attach nasal tubing to patients involves taping the portion of the tube that is not inserted within the patient's nose to the patient's face. Generally, surgical tape is used to adhere the nasal tubing to the nose of the patient. The patient's nose, however, can become irritated and sore as a result of repeated application and removal of the tape. This skin irritation can lead to painful infections and to prolonged post treatment care.

Another common method for securing nasal tubing to a patient involves positioning a tubal insert inside one of the patient's nostrils. The insert, however, causes irritation of the nasal membranes leading to mucous blockage. Another securement method involves placing a tube clamp beyond the patient's nose. This clamp suspends the nasal tubing as the tubing enters the patient's nose. The suspended tubing, however, experiences the pistoning action that causes discomfort and possible injury to the patient. Accordingly, health care personnel and patients require positioning of nasal tubing without irritating the skin or membranes of the nose.

SUMMARY OF THE DISCLOSURE

The present disclosure relates to a nasal device that adheres to the patient's nose without irritating the skin or membranes of the patient's nose. The nasal device comprises a nasal adapter having a lumen for guiding the nasogastric tubing within the nasal adapter as the tubing is inserted through the nasal passageway. The nasal device further has a flange and an adhesive member extending from the flange.

The health care personnel positions the flange to abut against the nare of the patient's nostril. The personnel adheres the extended adhesive member to the patient's nose. The positioning of the abutted flange and the adhesive member counters pistoning effects experienced by the tubing while the tubing is inserted into the lumen.

The foregoing features and advantages of the disclosure as well as presently preferred embodiments thereof will become more apparent from the reading of the following description in connection with the accompanying drawings.

BRIEF DESCRIPTION OF THE SEVERAL VIEWS OF THE DRAWINGS

In the accompanying drawings which form part of the specification.

Corresponding reference numerals indicate corresponding parts throughout the several figures of the drawings.

DESCRIPTION OF THE PREFERRED EMBODIMENT

The following detailed description illustrates the disclosure by way of example and not by way of limitation. The description clearly enables one skilled in the art to make and use the disclosure, describes several embodiments, adaptations, variations, alternatives, and uses of the disclosure, including what is presently believed to be the best mode of carrying out the disclosure.

Referring to the figures, a device for securing a fluid tube is disclosed. The device can be used for positioning, setting and securing a fluid tube to a patient. However, for purposes of illustration only, the device will be described as incorporating a device securing a nasogastric tube to the patient's nose. The device can be of any size to accommodate health care personnel and/or patients and/or fluid tubing of any size. Additionally, the device can be used on human patients or animal patients.

Nasogastric tubes are available in a variety of sizes and materials to properly insert or remove fluids from the patient. The selection of the nasogastric tube for any given patient depends on factors such as the size or age of the patient, the expected duration of the intubation, and the precise purpose for such intubation. In general, nasogastric tubes are commonly available in sizes ranging between 6 to 18 French (about 0.080 to 0.240 inches), and the materials from which they are formed may be relatively soft or of low durometer such as, for example, rubber, or considerably stiffer or of higher durometer, such as polyvinyl chloride. The stiffer materials are needed when the tube is to be used for aspirating purposes, since the material must be capable of resisting collapse when suction is applied. The softer materials are frequently used for feeding purposes, especially where relatively long-term intubation is anticipated. For the present disclosure, the term "tubing or tube" does not require any particular geometry and/or configuration.

Figure 1:
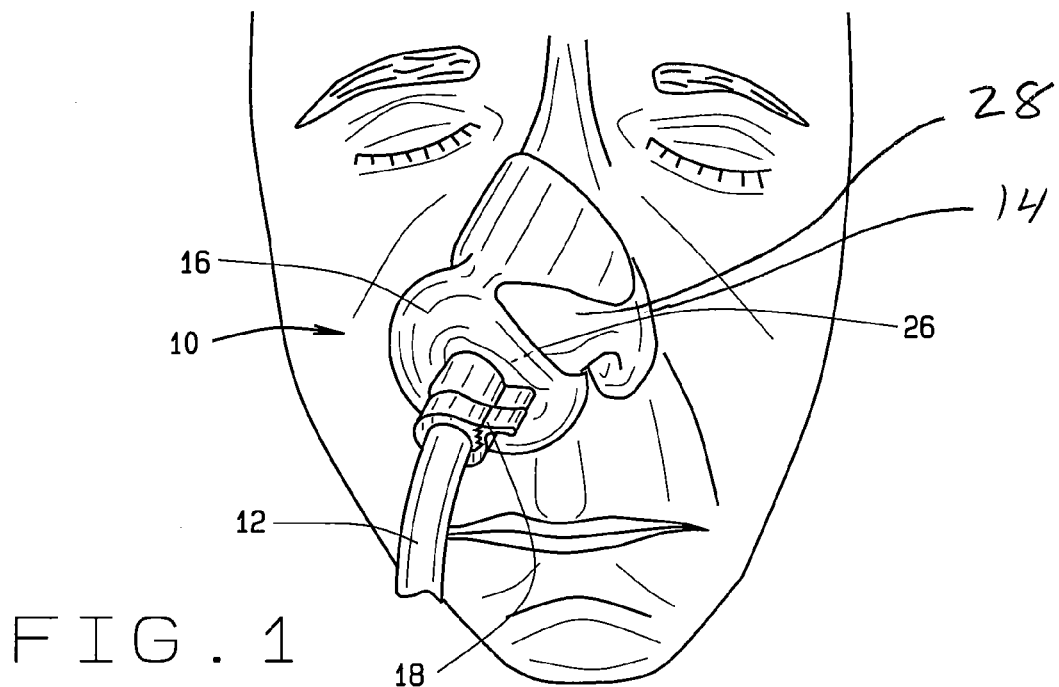
FIG. 1 is a front view of the nasal device of the present disclosure positioned on a patient's nose illustrating the device setting and positioning nasal tubing within the patient's nose.
Figure 2:
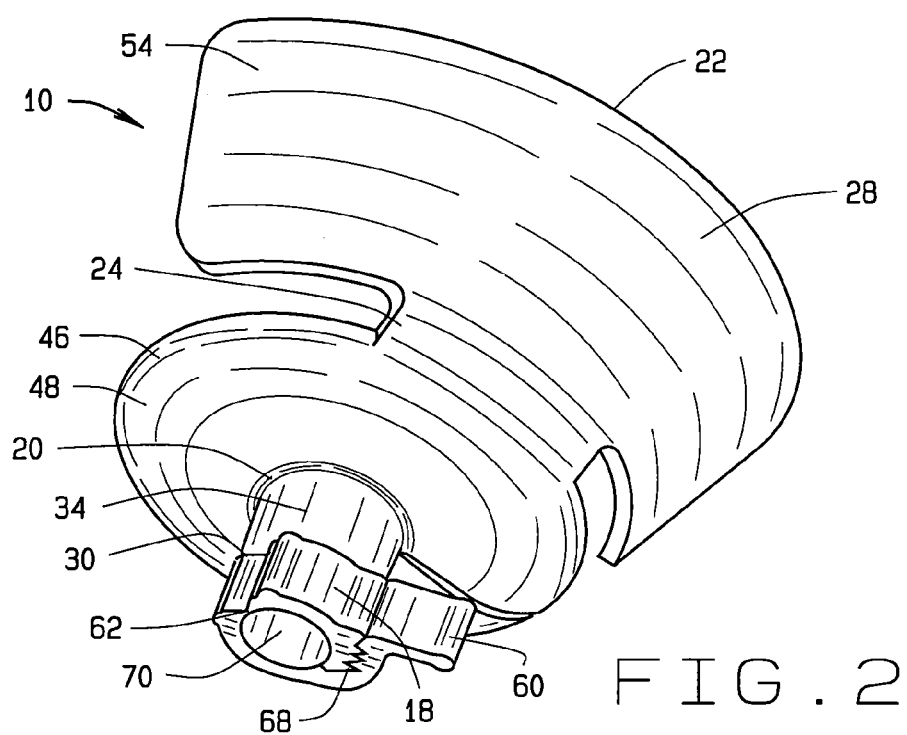
FIG. 2 is a front perspective view of the nasal device of FIG. 1 illustrating a nasal adaptor and connector constructed in accordance with and embodying the present disclosure.
Figure 3:
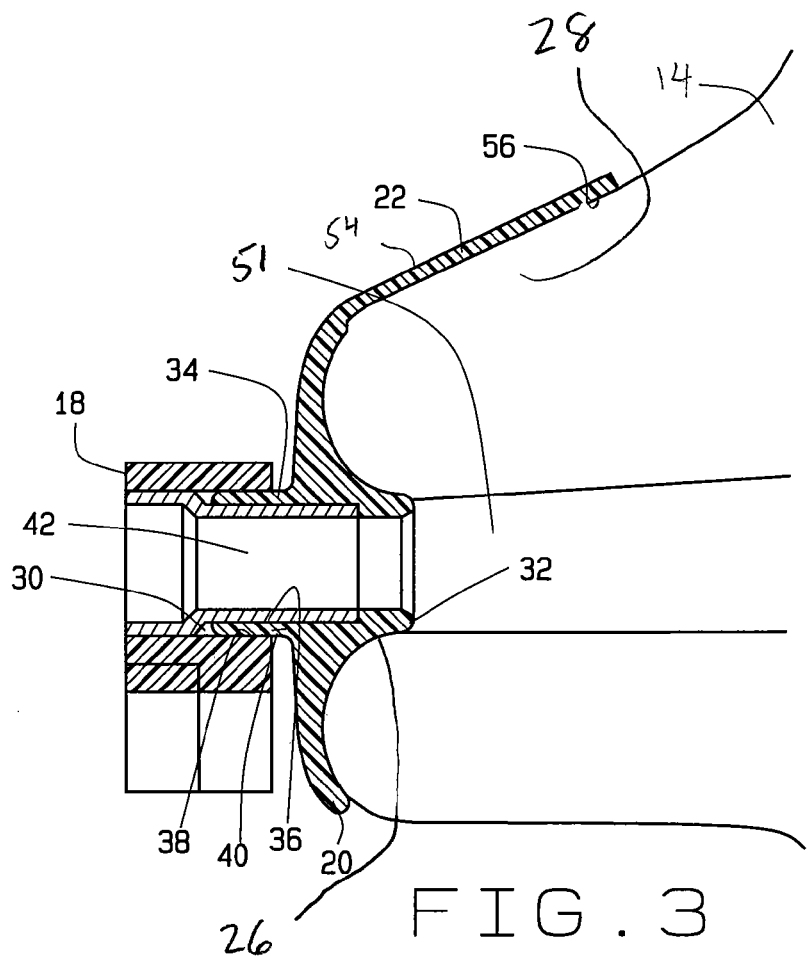
FIG. 3 is a side elevational view of the device positioned against a patient's nose.
Figure 4:
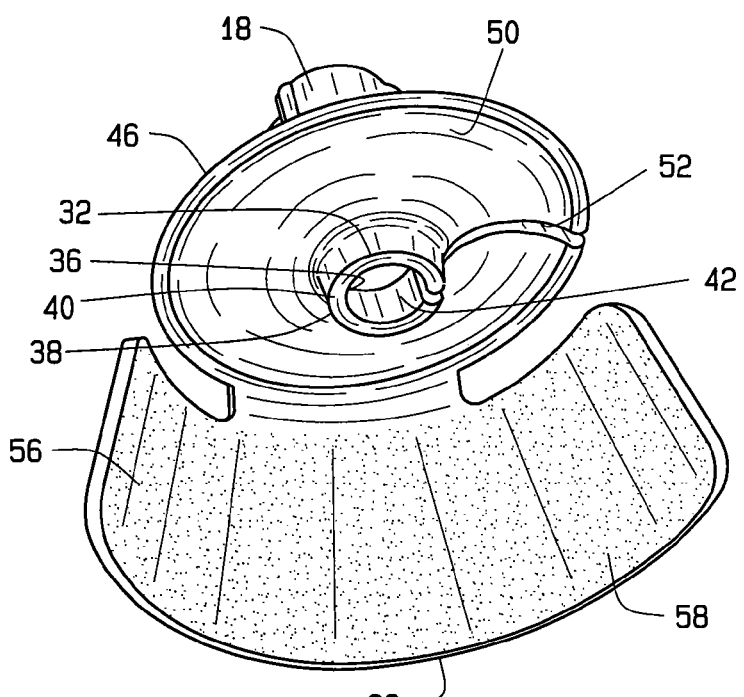
FIG. 4 is a rear perspective view of the nasal device of FIG. 2.
Figure 5:
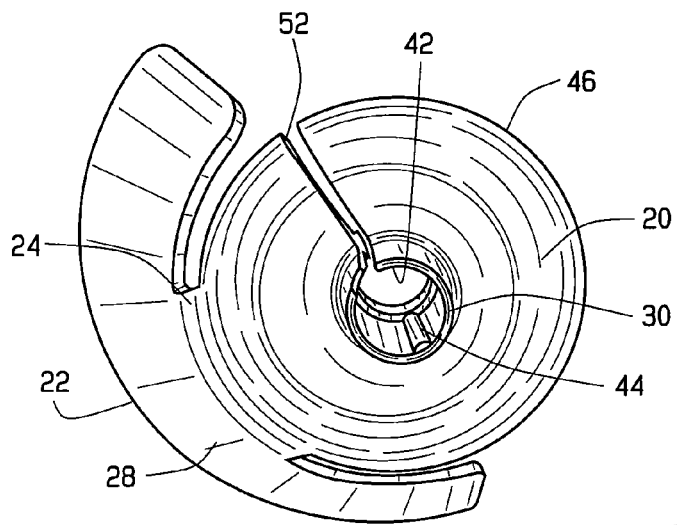
FIG. 5 is a front view of the nasal adaptor illustrating a flange and rib of the nasal adaptor.

Turning to FIGS. 1 and 2 and referring to FIGS. 3-5, a nasal device 10 of the present disclosure is shown. The nasal device 10 positions nasogastric tubing 12 within a patient's nose 14, without substantially irritating or eroding the skin of the patient's nose 14 or mucous membranes of the patient's nasal passageway 64. The device 10 minimizes or eliminates pistoning effects of the tube being applied to the patient's nasal passageway 64. Further, the device 10 eliminates the need of applying adhesive tape to the nasogastric tubing 12.

The nasal device 10 comprises a nasal adaptor 16 and a connector 18 which removably connects to the adaptor 16. The adaptor 16 of the device 10 may comprise a variety of materials such as, but not limited to, Synpreme® or other appropriate thermoplastic, elastomer material. Alternatively, the adaptor 16 can comprise a soft, flexible, porous material. Any soft, pliant fabric, whether woven or unwoven, that is sufficiently porous to allow for the passage of water vapor and gases therethrough, may be effectively used. Further, the adaptor 16 can have a variety of cross-sectional shapes such as elliptical, oval, circle, triangle, square, rectangular, winglike or other appropriate configuration.

The adaptor 16 comprises a first member 20, a second member 22 and a bridge 24 configured to connect together the first member 20 and the second member 22. The first member 20 is also configured to contact either of the nares 26 of the patient's nose 14. The second member 22 is configured to releasably attach to an alar wing 28 of the patient's nose 14. The nare 26 is generally construed as the exterior skin surface surrounding the nostril opening. The alar wing 28 is generally construed as the exterior side of the nose 14.

Turning to FIG. 3, the first member 20 includes a distal end 30, a proximal end 32 and a body 34 disposed there between. The first member 20 is configured to releasably hold the connector 18. The body 34 includes an inner wall 36, an outer wall 38 and a sidewall 40 connecting the inner wall 36 and the outer wall 38. The inner wall 36 defines a lumen 42 through the first member 20. The lumen 42 provides access for the nasal gastric tubing 12 to insert within and through the body 34 of the first member 20. Optimally, the lumen 42 is tubular shape or cylindrical shape having a uniformly sized diameter throughout. The lumen 42 may have other shapes and varying sized diameters throughout. In an embodiment, the lumen 42 has a diameter from about 0.1 inches to about 1 inch, and has a length from about 0.1 inch to about 2 inches. The dimensions are representative of an embodiment and not intended to limit the scope of the disclosure. Any lumen 42 length intended to position the nasogastric tubing 12 within the patient's nasal passageway 64 is intended to be within the scope of the disclosure.

The body 34 further includes a rib 44 (FIG. 5) positioned on the inner wall 36. The rib 44 is configured to stabilize the connector 18 as will be discussed. The rib 44 is positioned between the distal end 30 and the proximal end 32 and extends into the lumen 42. In an embodiment, the rib 44 has a half circle shape with ridges evenly distributed along the rib 44. Any stabilizing member, however, that can be employed to support/stabilize the connector 18 is intended to be within the scope of the disclosure.

The first member 20 also includes a flange 46 attached to the outer wall 38 of the body 34. As shown in the drawing 28s, the flange 46 extends outward from the body 34 at a position on the body 34 at about halfway between the proximal end 32 and the distal end 30. The flange 46, however, can be located at different positions along the body 34. In an embodiment, the flange 46 comprises a substantially circular configuration having an outer diameter from about 0.25 inches to about 2 inches.

The flange 46 has an outer side 48 facing the distal end 30 and has an inner side 50 facing the proximal end 32 of the body 34. The flange 46 is configured to assist the healthcare personnel in handling the nasal adaptor 16 since the healthcare personnel can easily grasp the inner and outer sides 46, 48 of the flange 46 with fingers or a medical clamp. The inner side 50 of the flange 46 is configured to contact the nare 26 of the patient's nostril 51 in which the nasogastric tubing 12 has been inserted. Since the inner side 50 does not enter the nostril 51 of the nose 14, the flange 46 does not irritate the mucus membranes of the nostril 51 in which the nasal tubing 12 has been inserted. The inner side 50 may include a local anesthetic (not shown) such as lidocaine disbursed throughout the back side 56. The inner side 50 may also include an antimicrol material (not shown) such as silver that inhibits growth of bacteria or viruses.

In an embodiment, the flange 46 and the body 34 include a slit 52 (FIG. 4) that extends through the flange 46 and through the body 34. The slit 52 extends from an outer edge off the flange 46 and through the inner wall 36 of the body 34. The slit 52 is in communication with the lumen 42 of the body 34. The slit 52 allows the flange 46 and the body 34 to surround the nasal gastric tubing 12. In particular, the slit 52 allows the flange 46 and the body 34 to be opened so as to insert a portion of the tubing 12 through the slit 52 and into the lumen 42.

Turning to FIGS. 2-4, the bridge 24 suspends the second member 22 from the first member 20. As shown, the bridge 24 connects with a portion of the flange 46 and connects with the second member 22. The bridge 24 has a length from about 0.25 inches to abut 1 inch. In an embodiment, the bridge 24 has a length of 0.625 inches. The bridge 24 has a width of about 1/32 of an inch to about 1/4 of an inch. In an embodiment, the bridge 24 has a width of about 1/8 of an inch. In an embodiment, the bridge 24 integrally connects with the flange 46 and with the second member 22. Alternatively, the bridge 24 can removably connect with the flange 46 and the second member 22 via adhesives. The bridge 24 is non-rigid to flexibly connect together the first member 20 and the second member 22. The bridge 24, however, can be rigid.

The second member 22 suspends from the bridge 24 so that the second member 22 contacts the either one or both of the alar wings 28 of the patient's nose 14. The second member 22 includes a front side 54 and a back side 56. The back side 56 is configured to cover portions of the patient's alar wing 28. The second member 22 can include a variety of shapes such as a semi-cylindrical shape or arc shape or wing 28 shape. The second member 22 has a length from about 0.25 inches to about 4 inches and a width from about 0.25 inches to about 4 inches. The back side 56 may include a layer or coating of pressure-sensitive adhesive such as a typical medical-grade acrylic adhesive as commonly used in the manufacture of adhesive tapes for medical use. The second member 22 may also include a local anesthetic (FIG. 4) such as lidocaine disbursed throughout the back side 56. In another embodiment, the back side 56 may include an anti-microl material (not shown) such as silver that inhibits growth of bacteria or viruses.

A cushioning layer (not shown) of a soft, tacky, and deformable skin barrier material (such as karaya or a barrier composition) may extend along the back side 56 of the second member 22. Also, the adhesive undersurface of the back side 56 could be covered with a strippable release layer of paper (not shown) or other suitable material to protect the back side 56 until use of the product is desired.

The second member 22 is positioned over the alar wing 28 of the nose 14 so that the back side 56 contacts the alar wing 28 of the nose 14. Since the second member 22 contacts large portions of the nose 14, the back side 56 is distributed over the alar wing 28 and does not substantially irritate and/or erode a specific point on the outside of the nose 14. Further, since the second member 22 does not enter the nose 14, the second member 22 does not irritate the mucus membranes of the nostril 51 in which the nasal tubing 12 has been inserted.

As shown in FIG. 4, the bridge 24 extends the second member 22 beyond the flange 46 of the first member 20. The inner side 50 of the flange 46 is positioned against the nare 26 of the nostril 51 and in an angular relationship with respect to the second member 22. In an embodiment, the flange 46 is positioned substantially perpendicular with the second member 22. The back side 56 is positioned forward or beyond the nare 26 as measured from the first member 20. The flange 46 of the first member 20 is positioned rearward from the nare 26 as measured from the second member 22. The lumen 42, however, remains substantially planar with the nostril 51 of the nose 14 along an axis 62 of the nasal passageway 64.

Figure 6:
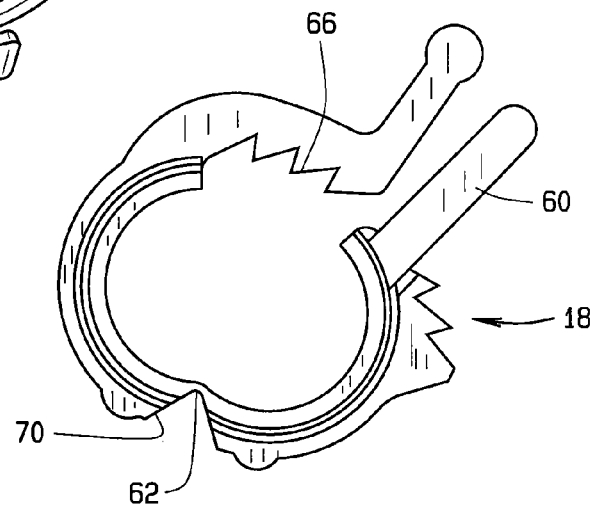
FIG. 6 is a front view of the connector of FIG. 2 illustrating the connector in an open position.
Figure 7:
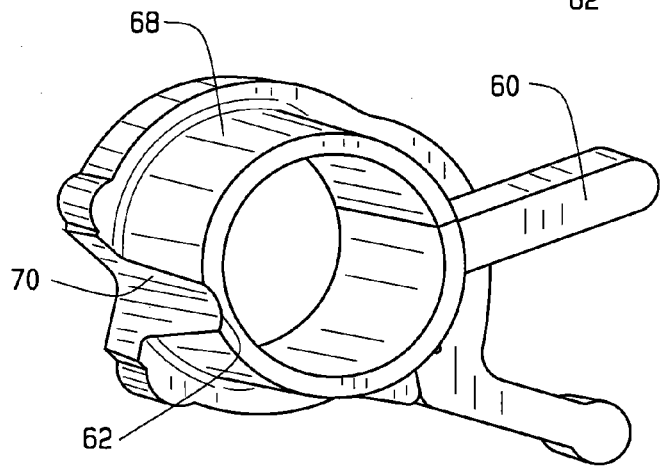
FIG. 7 is a rear perspective view of the connector of FIG. 6 illustrating the connector in a closed position.

Returning to FIG. 1 and referring to FIGS. 6 and 7, the connector 18 is configured to removably insert through the distal end 30 of the body 34 and within the lumen 42. In an embodiment, the connector 18 is configured to pressurably insert within the body 34 to fit within the lumen 42. The connector 18 is configured to connect to the nasogastric tubing 12 to secure the nasogastric tubing 12 within the nasal adaptor 16. Any connecting member that can be employed to connect to the body 34 and to the nasal gastric tubing 12 is intended to be within the scope of the disclosure. The connector 18 can be constructed in any acceptable manner and shape that allows for the connection of the body 34 to the nasal gastric tubing 12.

In an embodiment, the connector 18 comprises clamping arms 60 pivotally connected to each other along a pivot axis 62. Clamping arms 60 are configured to pivotally receive a portion of the nasal tube. The pivotally-mounted arms 60 may be swung between an open position such as shown in FIG. 5 and a closed position illustrated in FIGS. 2 and 7. In the closed position, the arms 60 form a passageway 64 through the connector 18.

The arms 60 include adjustable fastener 66s for selectively and releasably locking the arms 60 in any of a plurality of closed positions. The plurality of closed positions correlates to a variety of sizes for the formed passageway 64 to surround a specific size of tubing 12. The fasteners 66 may take the form of intermeshing ratchet teeth provided by the respective arms 60. Arm includes a series of teeth disposed opposite from the pivot axis 62 of arms 60. Arm has at least one tooth adapted to mate with any of the teeth of arm. Normally the arm assumes a raised or latching position; but, when the tip of one of the arms 60 is urged away from the other arm, the ratchet teeth are disengaged and the arms 60 may be shifted into the open positions.

Each arm has a stem 68 extending outward from the respective teeth. As shown, the stems 68 connect together along the pivot axis 62. The arms 60 and the stems 68 form a channel 70 around the pivot axis 62. The channel 70 is configured to receive the rib 44 that extends into the lumen 42. During insertion of the connector 18 into the distal end 30 of the lumen 42, the rib 44 aligns with the channel 70 to assist stabilizing the connector 18 in the lumen 42. Alternatively, the stems 68 of the connector 18 may include an adhesive layer (not shown) that attaches to the inner wall 36 of the lumen 42. The adhesive layer can assist in securing the connector 18 to the lumen 42.

During use, the nasal adaptor 16 of the present disclosure assists in positioning and securing the nasal gastric tubing 12 within the patient's nose 14 without irritating or eroding the skin of the patient's nose 14. Additionally, during operation, the nasal adaptor 16 minimizes or eliminates pistoning effects of the tube being applied to the patient's mucous membrane of the nostril 51. During insertion of the nasal tubing 12, the healthcare personnel positions the patient on the side of the bed or chair and measures the nasal gastric tubing 12 from the tip of the patient's nose 14 to the earlobe and down to the breast bone. The healthcare personnel then marks this point on the nasal gastric tubing 12. This length allows the tube to insert within the gastrinol/intestinal tract and into the stomach.

The healthcare personnel grasps the flange 46 of the first member 20 to expose the slit 52 to the tubing 12. A portion of the tubing 12 is then inserted through the slit 52 of the flange 46 and the body 34 to position the tubing 12 within the lumen 42. Once the nasal gastric tubing 12 is inserted within the lumen 42, the personnel may insert the end of the tubing 12 beyond the lumen 42 and into the patient's body 34 via the patient's nostril 51. The personnel lubricates the nasal gastric tube and inserts the tubing 12 through the nostril 51. The patient may take sips of water to assist passing the tubing 12 into the gastric and intestinal track.

When the tubing 12 reaches the marked point, the connector 18 arms 60 are moved to the position to removably clamp around the tubing 12. The connector 18 arms 60 are moved to the open position to accept the tubing 12 within the passageway 64 formed by the connector 18 arms 60.

The healthcare personnel adhesively connects the back side 56 of the second member 22 against the alar wing 28 of the patient's nose 14. The back side 56 remains free from entering the patient's nose 14 while the nasogastric tubing 12 is positioned within the patient's nose 14. Since the second member 22 extends beyond the flange 46, the second member 22 may contact both alar wings 28 of the patient's nose 14. The health care personnel then minimally inserts the proximal end 32 of the body 34 of the first member 20 into one of the patient's nostril 51. This positioning abuts the inner side 50 of the flange 46 against the nare 26 of the associated nostril 51. As shown, the flange 46 is angularly positioned with respect to the second member 22. In an embodiment, the flange 46 is positioned substantially perpendicular with respect to the second member 22.

To check the location of the nasogastric tubing 12, the personnel places a stethoscope over the patient's stomach and with a syringe quickly inserts 3 to 5 cc's of air into the tube while listening with a stethoscope for a "pop". The pop represents air rushing into the stomach to signal proper insertion of the nasogastric tubing 12.

In an alternative use, the healthcare personnel may apply local anesthetic or the medicinal layer to the back side 56 of the second member 22 prior to positioning the second member 22 against the alar wing 28 of the patient's nose 14. Alternatively, the healthcare personnel may apply local anesthetic or the medicinal layer to the inner side 50 of the flange 46 of the first member 20 prior to positioning the inner side 50 against the nare 26 of the patient's nose 14.

While the tube delivers or aspirates fluid into or out of the patient's stomach, the tube may experience a pistoning action by moving forward or backward within the nasal passageway 64 and mucous membranes. The angular relationship of the first member 20 and the second member 22 minimizes or eliminates the adverse piston effects applied to the patient's nostril 51. In particular, if the tube moves backward in a direction out of the nostril 51 (i.e., during fluid aspiration by the tube), the second member 22 counters this backward movement. Since the second member 22 attaches to the alar wing 28 in an angular position forward the first member 20, the adhesion of the second member 22 to the alar wing 28 resists backward movement of the tubing 12 out of the nostril 51. Conversely, if the tube moves forward in a direction into the lumen 42 (i.e., during fluid delivery), the first member 20 counters or resists this forward movement since the inner side 50 of the flange 46 contacts the nare 26 of the nostril 51.

The angular relation of the first member 20 and the second member 22 as positioned on the nare 26 and alar wing 28 counters movement by the tube. The connector 18 also secures the nasal tube to the first member 20 to minimize movement of the tubing 12. This angular relation minimizes or eliminates the pistoning effects of the nasal tubing 12 applied to the mucous membranes.

In view of the above, it will be seen that features of the disclosure are achieved and other advantageous results are obtained. As various changes could be made in the above constructions without departing from the scope of the disclosure, it is intended that all matter contained in the above description or shown in the accompanying drawings shall be interpreted as illustrative and not in a limiting sense. The dimensions disclosed herein are representative of an embodiment and not intended to limit the scope of the disclosure.

The invention claimed is:

1. A nasal device for positioning nasogastric tubing within a patient's nose, comprising:
   an adapter having a proximal end, a distal end and body disposed between the proximal end and the distal end, the body having an inner surface defining a lumen that is configured to guide the nasogastric tubing within a nostril of the patient's nose, the nasal adapter further having an ellipsoidal flange extending outward from the body, the ellipsoidal flange having an outer edge, the ellipsoidal flange being configured to contact a nare of the patient's nose;
   a slit extending from the outer edge of the flange to the inner surface of the body; and
   a member operatively connected to the ellipsoidal flange, the member having a front side and a back side wherein the back side removably connects to an alar wing of the patient's nose in an angular relation with respect to the ellipsoidal flange.

2. The nasal device of claim 1 wherein the ellipsoidal flange has an outer side and an inner side, the inner side being positioned to contact the nare of the patient's nose.

3. The nasal device of claim 2 wherein the ellipsoidal flange is configured to resist movement of the nasogastric tubing into the nostril.

4. The nasal device of claim 1 wherein the back side is positioned substantially perpendicular with respect to the ellipsoidal flange.

5. The nasal device of claim 4 wherein the back side is configured to resist movement of the nasogastric tubing out of the nostril.

6. The nasal device of claim 1 further comprising a connector attached to the distal end of the body, the connector being configured to clamp the nasogastric tubing.

7. The nasal device of claim 1 further comprising a bridge configured to operatively connect together the body and the member.

8. The nasal device of claim 1 further compromising a medicinal layer positioned on the back side of the body.

9. The nasal device of claim 8 wherein the medicinal layer includes a local anesthetic dispersed throughout.

10. The nasal device of claim 8 wherein the medicinal layer includes an antimicrobial material dispersed throughout.

11. The nasal device of claim 1 wherein the nasal adaptor and the member comprises a thermoplastic elastomer.

12. A nasal device for positioning nasogastric tubing within a patient's nose, comprising:
    an adapter having a proximal end, a distal end and body disposed between the proximal end and the distal end, the body having an inner surface defining a lumen that is configured to guide the nasogastric tubing within a nostril of the patient's nose, the nasal adapter further having an ellipsoidal flange extending outward from the body, the ellipsoidal flange having an outer edge, wherein the ellipsoidal flange is configured to contact a nare of the patient's nose;
    a slit extending from the outer edge of the flange to the inner surface of the body; and
    a member operatively connected to the ellipsoidal flange, the member having a front side and a back side wherein the back side removably connects to an alar wing of the patient's nose in a substantially perpendicular relation with respect to the ellipsoidal flange such that the ellipsoidal flange is positioned on the nare to resist movement of the nasogastric tubing into the nostril and the back side is positioned on the alar wing to resist movement of the nasogastric tubing out of the nostril.

13. The nasal device of claim 12 wherein the ellipsoidal flange is positioned to remain free from entering the nostril.

14. The nasal device of claim 12 wherein the back side is positioned to remain free from entering the patient's nose.

15. The nasal device of claim 12 further comprising a connector attached to the distal end of the body, the connector being configured to clamp the nasogastric tubing.

16. The nasal device of claim 12 further comprising a bridge configured to operatively connect together the body and the member.

17. A method of positioning a nasal adapter in communication with a patient's nose for inserting nasogastric tubing within the patient's nostril, comprising:
    inserting the nasogastric tubing through an outer edge of an ellipsoidal flange;
    inserting the nasogastric tubing through an inner surface of a body;
    removeably positioning the body around the nasogastric tubing;
    inserting the nasogastric tubing within a lumen of the body;
    inserting the nasogastric tubing that extends beyond the body into the patient's nostril;

positioning a first member of the nasal adapter against a nare of the nostril; and positioning a second member of the nasal adapter against an alar wing of the nose wherein the positioning of the first member and the positioning of the second member resists movement of the nasogastric tubing that is positioned within the nostril.

18. The method of claim 17 wherein the positioning of the first member and the second member comprises positioning the first member and the second member in an angular relationship with respect to each other.

* * * * *